United States Patent
Ogihara

(10) Patent No.: US 9,320,852 B2
(45) Date of Patent: *Apr. 26, 2016

(54) FLUID TRANSPORT DRIVING UNIT AND COMPUTER READABLE MEDIUM

(71) Applicant: PRIMETECH CORPORATION, Tokyo (JP)

(72) Inventor: Ryosuke Ogihara, Chiba (JP)

(73) Assignee: PRIMETECH CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/937,147

(22) Filed: Jul. 8, 2013

(65) Prior Publication Data

US 2013/0296774 A1 Nov. 7, 2013

Related U.S. Application Data

(63) Continuation of application No. PCT/JP2012/004760, filed on Jul. 26, 2012.

(30) Foreign Application Priority Data

Jul. 28, 2011 (JP) .................. 2011-165699

(51) Int. Cl.
*A61M 5/142* (2006.01)
*A61M 5/168* (2006.01)
(Continued)

(52) U.S. Cl.
CPC ........... *A61M 5/172* (2013.01); *A61M 5/14244* (2013.01); *F04B 43/082* (2013.01);
(Continued)

(58) Field of Classification Search
CPC .............. A61M 2005/14268; A61M 2205/12; A61M 2205/3569; A61M 5/14228; A61M 5/14232; A61M 5/14244; A61M 5/16827; A61M 5/172; A61M 5/1723; F04B 43/082; F04B 43/1261; F04B 49/06; F04B 43/1253; F04B 43/1276; F04B 43/02; F04B 43/042

USPC .................................. 604/131, 151
See application file for complete search history.

(56) References Cited

U.S. PATENT DOCUMENTS 3,736,930 A * 6/1973 Georgi ........................... 604/67
4,457,751 A 7/1984 Rodler
(Continued)

FOREIGN PATENT DOCUMENTS

JP  H01-249064 A  10/1989
JP  H06-205829 A  7/1994
(Continued)

OTHER PUBLICATIONS

International Search Report for International Application No. PCT/JP2012/004760, issued by the Japanese Patent Office on Oct. 16, 2012.
(Continued)

*Primary Examiner* — Nathan R Price
*Assistant Examiner* — Weng Lee

(57) ABSTRACT

There are cases where a fluid transport apparatus cannot accurately discharge a set discharge amount of fluid, due to individual differences in components of the fluid transport apparatus, such as the diameter of an opening of an elastic tube. Therefore, in a fluid transport apparatus including a fluid transport cartridge and a fluid transport driving unit that are separable from each other, the fluid transport driving unit comprises a driving section that causes a drive mechanism to operate to transport fluid filling a transport path of an attached fluid transport cartridge to a discharge opening of the transport path; a receiving section that receives a characteristic value measured in advance for each of a plurality of the fluid transport cartridges; and a control section that controls the driving section based on the characteristic values received by the receiving sections.

7 Claims, 12 Drawing Sheets

(51) Int. Cl.
  *F04B 43/12* (2006.01)
  *F04B 43/08* (2006.01)
  *A61M 5/172* (2006.01)
  *F04B 49/06* (2006.01)

(52) U.S. Cl.
  CPC ............ *F04B43/1261* (2013.01); *F04B 49/06* (2013.01); *A61M 5/14228* (2013.01); *A61M 5/14232* (2013.01); *A61M 5/16827* (2013.01); *A61M 5/1723* (2013.01); *A61M 2005/14268* (2013.01); *A61M 2205/12* (2013.01); *A61M 2205/3569* (2013.01)

(56) References Cited

U.S. PATENT DOCUMENTS

| | | | | |
|---|---|---|---|---|
| 4,741,736 | A | * | 5/1988 | Brown ..................... 604/134 |
| 5,205,819 | A | * | 4/1993 | Ross et al. ................. 604/67 |
| 5,695,473 | A | | 12/1997 | Olsen |
| 5,840,058 | A | * | 11/1998 | Ammann et al. ............. 604/30 |
| 7,819,643 | B2 | * | 10/2010 | Miyazaki et al. ......... 417/477.3 |
| 2003/0130616 | A1 | * | 7/2003 | Steil et al. .................. 604/66 |
| 2012/0265125 | A1 | * | 10/2012 | Kawamura .................. 604/66 |

FOREIGN PATENT DOCUMENTS

| | | |
|---|---|---|
| JP | H06-317257 A | 11/1994 |
| JP | H11-503939 A | 4/1999 |
| JP | 2000-54967 A | 2/2000 |
| JP | 2007-138775 A | 6/2007 |
| JP | 2009-279425 A | 12/2009 |
| JP | 2010-48121 A | 3/2010 |
| JP | 2011-111989 A | 6/2011 |

OTHER PUBLICATIONS

Office Action for Japanese Patent Application No. 2011-165699, issued by the Japanese Patent Office on Dec. 25, 2012.

Notification of First Office Action for Chinese Application No. 201280006206.4, issued by the State Intellectual Property Office of China on Apr. 4, 2014.

International Preliminary Report on Patentability of International Application No. PCT/JP2012/004760, issued by the International Bureau of WIPO on Feb. 6, 2014.

Extended European Search Report for European Patent Application No. 12 81 7535.3, issued by the European Patent Office on May 4, 2015.

* cited by examiner

FLUID TRANSPORT DRIVING UNIT AND COMPUTER READABLE MEDIUM

The contents of the following patent applications are incorporated herein by reference:
No. 2011-165699 filed in JP on Jul. 28, 2011, and
PCT/JP2012/004760 filed on Jul. 26, 2012

BACKGROUND

1. Technical Field

The present invention relates to a fluid transport driving unit and computer readable medium storing thereon a fluid transport driving unit control program.

2. Related Art

Patent Document 1 describes a peristaltically-driven fluid transport apparatus that transfers fluid through an elastic tube by pressing the elastic tube with a plurality of fingers sequentially from an upstream side to a downstream side by rotation of a cam.
Patent Document 1: Japanese Patent Application Publication No. 2011-111989

In the fluid transport apparatus described above, a set discharge amount of the fluid is discharged through the elastic tube. However, there are cases where the set discharge amount of fluid is not accurately discharged, due to individual differences in components of the fluid transport apparatus, such as the diameter of the tube openings.

SUMMARY

The fluid transport driving unit of the present invention comprises a driving section that causes a drive mechanism to operate to transport fluid filling a transport path of an attached fluid transport cartridge to a discharge opening of the transport path; a receiving section that receives a characteristic value measured in advance for each of a plurality of the fluid transport cartridges; and a control section that controls the driving section based on the characteristic values received by the receiving sections.

In the fluid transport driving unit, the characteristic values may be correction values for correcting variation in discharge amount of the fluid with respect to a driving amount of the driving section. The characteristic values may be correction values for correcting variation based on individual differences among elastic tubes for forming the transport path.

In the fluid transport driving unit, the driving section may be a cam body that moves a pressing pin pressing the elastic tube from the outside, and the control section may control a rotation amount of the cam body based on the correction values.

The fluid transport driving unit may comprise a position fixing member that houses the cam body, is shaped as an arc relative to a rotational center of the cam body, and fixes a position relative to the fluid transport cartridge. The fluid transport driving unit may comprise a pressure sensor that measures pressure of the elastic tube. In the fluid transport driving unit, the control section may control the driving section based on output of the pressure sensor.

The fluid transport driving unit may comprise a biometric information acquiring section that acquires biometric information of a subject to which the fluid transport driving unit is attached, and the control section may control the driving section based on the biometric information.

The fluid transport driving unit may comprise a communicating section that wirelessly acquires a setting condition for controlling the driving section, and the control section may control the driving section based on the setting condition.

A computer readable medium storing thereon a fluid transport driving unit control program according to the present invention causes a computer to receive a characteristic value measured in advance for an attached fluid transport cartridge; and control a driving section, which causes a drive mechanism to operate to discharge fluid filling a transport path of the fluid transport cartridge to a discharge opening, based on the received characteristic value.

The summary clause does not necessarily describe all necessary features of the embodiments of the present invention. The present invention may also be a sub-combination of the features described above.

DESCRIPTION OF EXEMPLARY EMBODIMENTS

Hereinafter, an embodiment of the present invention will be described. The embodiment does not limit the invention according to the claims, and all the combinations of the features described in the embodiment are not necessarily essential to means provided by aspects of the invention.

Figure 1:
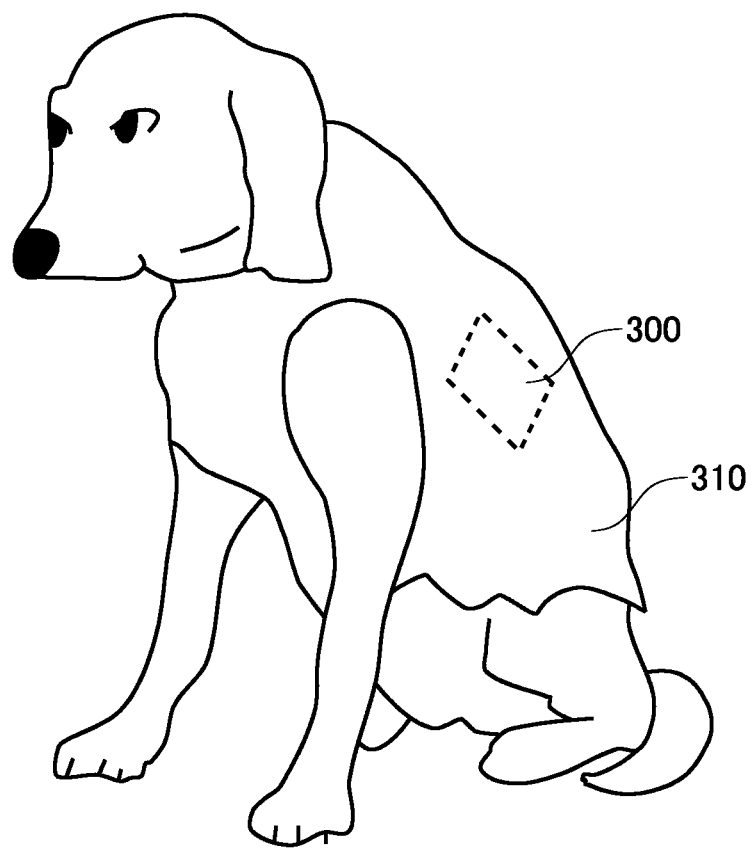
FIG. 1 shows an exemplary usable form of a fluid transport apparatus according to the present embodiment.

FIG. 1 shows an exemplary usable form of a fluid transport apparatus 300 according to an embodiment of the present invention. The fluid transport apparatus 300 is fixed to test clothing 310 that is worn by a test animal serving as a test subject, such as a dog or monkey. The fluid transport apparatus 300 injects fluid such as medicine into the body of the test animal, in units of a discharge amount determined according to predetermined setting conditions. The setting conditions are programmed to include conditions such as discharge start time, a discharge ratio indicating the discharge amount per unit time, discharge duration, and discharge interval. If necessary, the setting conditions can be changed by remote operation via wireless communication.

The fluid is not limited to fluids such as medicine, saline solution, and nutrient solution, and may be gas or gel that includes the component to be discharged. The fluid transport apparatus 300 has a size that enables a medium-sized pet or test animal to move while wearing the fluid transport apparatus 300, and therefore the subject wearing the fluid transport apparatus 300 is not limited to a test animal, and can be a human instead. By having a human wear the fluid transport apparatus 300, medicinal fluid can be provided periodically or at planned times to living tissue, such as blood vessels or muscles, for example.

Figure 2:
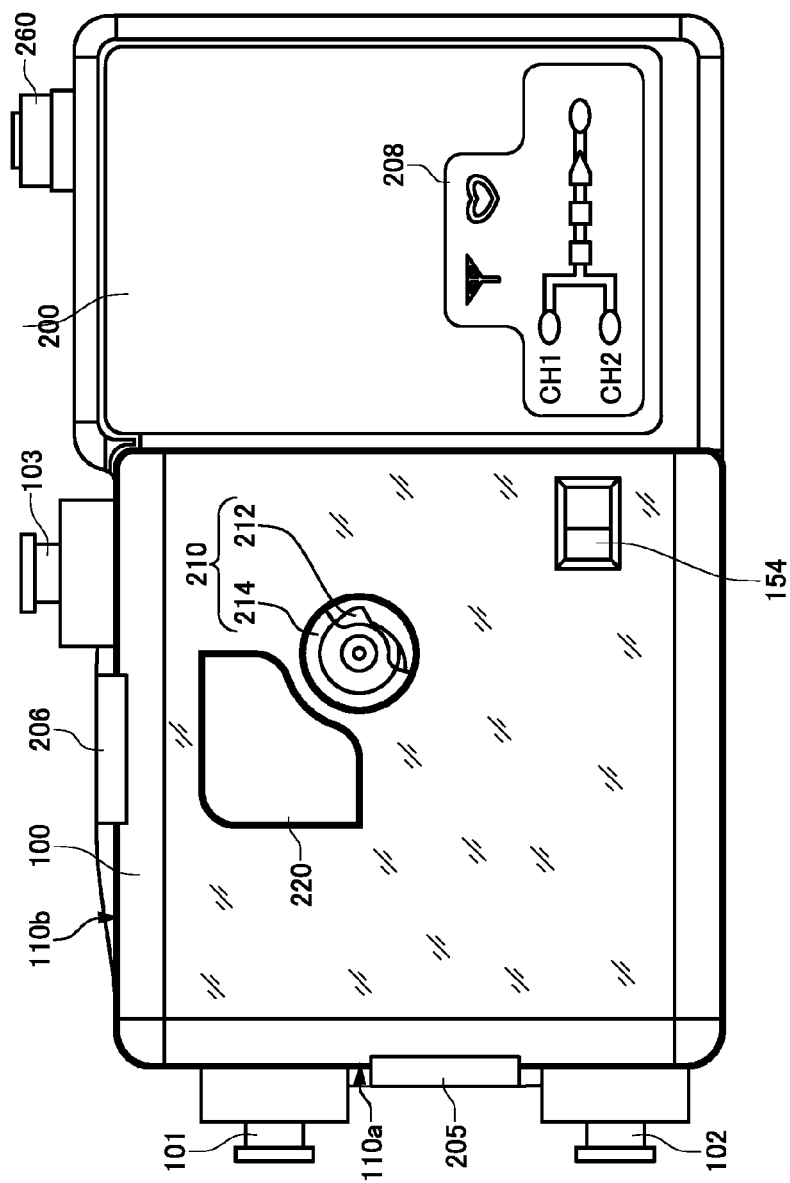
FIG. 2 is an overhead view of the fluid transport apparatus according to the present embodiment.

FIG. 2 is an overhead view of the fluid transport apparatus 300. The fluid transport apparatus 300 includes a fluid transport cartridge 100 and a fluid transport driving unit 200. The fluid transport apparatus 300 can selectively discharge two types of fluid. The fluid transport cartridge 100 is fixed in a detachable manner to the fluid transport driving unit 200. The fluid transport cartridge 100 includes a first fluid inflow portion 101, a second fluid inflow portion 102, and a fluid discharge portion 103. The first fluid inflow portion 101 is connected to an external first reservoir that contains a first fluid. The second fluid inflow portion 102 is connected to a second reservoir that contains a second fluid. The fluid discharge portion 103 is connected to an inflow tube for introducing the first fluid and the second fluid into the body of the test animal.

The fluid transport driving unit 200 includes a cam unit 210. The cam unit 210 includes a cam body 212 that provides rotational drive and a cam cover 214 that houses the cam body 212. The cam unit 210 is a drive mechanism that guides the first fluid or the second fluid from the first fluid inflow portion 101 or the second fluid inflow portion 102 to the fluid discharge portion 103. The cam unit 210 of the fluid transport driving unit 200 also functions to fix the position of the fluid transport cartridge 100. The cam cover 214 of the cam unit 210 is shaped as an arc around a rotational center, and when the fluid transport cartridge 100 is to be fixed, the cam cover 214 sets the position of the fluid transport cartridge 100 relative to the fluid transport driving unit 200.

Furthermore, the fluid transport driving unit 200 includes an input terminal 260 for acquiring biometric information relating to the test animal. The biometric information is information relating to an electrocardiogram or information relating to the blood pressure of the test animal, for example. The biometric information may be used to control discharge of the fluid. If the discharge of the fluid is not controlled according to the biometric information, the input terminal 260 need not be provided. The fluid transport driving unit 200 includes a first hook 205 and a second hook 206 for fixing the fluid transport cartridge 100. The first hook 205 fixes one edge 110a of the fluid transport cartridge 100 between the first fluid inflow portion 101 and the second fluid inflow portion 102. The second hook 206 fixes one edge 110b of the fluid transport cartridge 100 where the fluid discharge portion 103 is provided. The fluid transport cartridge 100 and the fluid transport driving unit 200 are fixed by the locking member 154. In this way, by fixing the fluid transport cartridge 100 on two edges together with the locking member 154, the fluid transport cartridge 100 is prevented from falling from the fluid transport driving unit 200. Furthermore, when the fluid transport cartridge 100 is to be removed, the locking member 154 is released and the first hook 205 is pressed by the thumb of the right hand, for example, while pressing the second hook 206 with another finger of the right hand, and the fluid transport cartridge 100 can then be removed by the left hand. Accordingly, the fluid transport cartridge 100 can be easily detached from the fluid transport driving unit 200. In this way, by including different fixing functions such as the first hook 205, the second hook 206, and the locking member 154 in the fluid transport apparatus 300, when the fluid transport apparatus 300 is worn by a primate such as a monkey, the fluid transport cartridge 100 can be prevented from falling off as a result of the primate touching the fluid transport cartridge 100.

Figure 3:
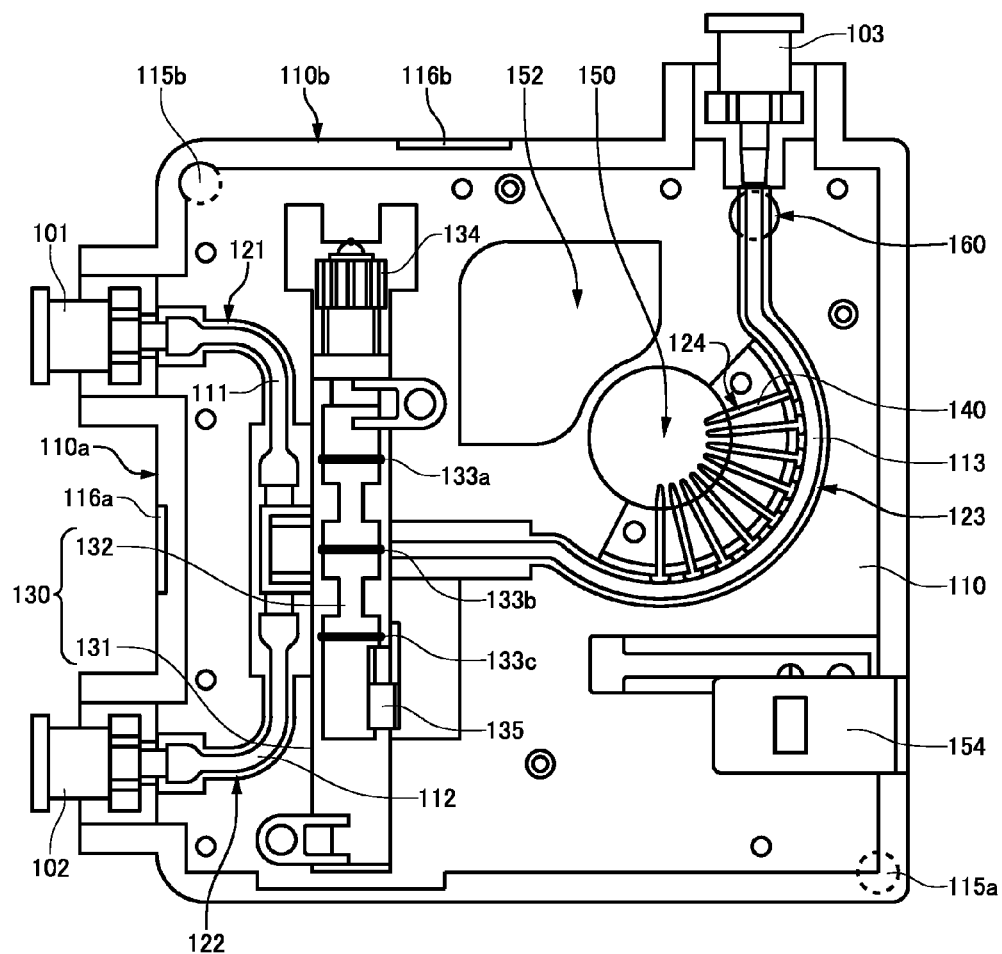
FIG. 3 is a schematic view of the internal structure of the fluid transport cartridge according to the present embodiment.

FIG. 3 is a schematic view of the internal structure of the fluid transport cartridge 100. The fluid transport cartridge 100 includes an external packaging member 110, a first elastic tube 111, a second elastic tube 112, a switching valve 130, a threaded shaft 134, a third elastic tube 113, and a plurality of pressing pins 140. The external packaging member 110 houses the first elastic tube 111, the second elastic tube 112, the switching valve 130, the threaded shaft 134, the third elastic tube 113, and the plurality of pressing pins 140. In the external packaging member 110, at least the outward-facing surface that is opposite the inward-facing surface facing the fluid transport driving unit 200 is transparent. The locking member 154 for fixing the fluid transport cartridge 100 to the fluid transport driving unit 200 is provided in the external packaging member 110. The contour of the external packaging member 110 as seen from the outward-facing surface or inward-facing surface of the fluid transport cartridge 100 is substantially rectangular, in the portion not including the first fluid inflow portion 101, the second fluid inflow portion 102, and the fluid discharge portion 103, and is fixed to the fluid transport driving unit 200 at two edges of the rectangular contour. Among these two edges, the edge 110a is provided between the first fluid inflow portion 101 and the second fluid inflow portion 102, and the edge 110b is provided with the fluid discharge portion 103. The external packaging member 110 includes a first fastening portion 116a to which the first hook 205 is fixed, on the edge 110a. The external packaging member 110 includes a second fastening portion 116b to which the second hook 206 is fixed, on the edge 110b.

The first elastic tube 111 forms a first fluid path that is arranged along a first groove 121 formed in the external packaging member 110. One end of the first elastic tube 111 is connected to the first fluid inflow portion 101, and the other end is connected to the switching valve 130. The first elastic tube 111 delivers the first fluid introduced through the first fluid inflow portion 101 from the first reservoir to the switching valve 130. The second elastic tube 112 forms a second fluid path that is arranged along a second groove 122 formed in the external packaging member 110. One end of the second elastic tube 112 is connected to the second fluid inflow portion 102, and the other end is connected to the switching valve 130. The second elastic tube 112 delivers the second fluid introduced through the second fluid inflow portion 102 from the second reservoir to the switching valve 130. The third elastic tube 113 forms a third fluid path that is arranged along a third groove 123 formed in the external packaging member 110. One end of the third elastic tube 113 is connected to the switching valve 130, and the other end is connected to the fluid discharge portion 103. The third elastic tube 113 delivers the first fluid and the second fluid introduced through the switching valve 130 to the fluid discharge portion 103. The first fluid inflow portion 101, the second fluid inflow portion 102, and the fluid discharge portion 103 may be Luer-Lok style connectors, which are easily detachable.

The switching valve 130 guides one of the first fluid and the second fluid to the fluid discharge portion 103. The switching valve 130 includes a cylinder 131, a piston 132, and O-rings 133a, 133b, and 133c. The cylinder 131 is connected to the first elastic tube 111, the second elastic tube 112, and the third elastic tube 113. The piston 132 engages through the O-rings 133a, 133b, and 133c in the cylinder 131 to move between a first state in which the first fluid is guided from the first elastic tube 111 to the third elastic tube 113 and a second state in which the second fluid is guided from the second elastic tube 112 to the third elastic tube 113. The threaded shaft 134 engages within the piston 132, and forms a ball screw together with the piston 132 and the O-rings 133a, 133b, and 133c. In response to rotation of the threaded shaft 134 on a central axis, the piston 132 and the O-rings 133a, 133b, and 133c slide along the inner wall of the cylinder 131, thereby moving between the first state and the second state.

The piston 132 includes a detector 135. The detector 135 protrudes from an opening formed in the inward-facing surface of the external packaging member 110, through an opening formed in the cylinder 131. A position sensor of the fluid transport driving unit 200 detects the detector 135, thereby detecting the position of the piston 132. The detection results are provided to the fluid transport driving unit 200, and a LED display section 208 of the fluid transport driving unit 200 displays the detection results. By viewing the state of the LED display section 208, a user can confirm which of the first fluid and the second fluid is selected as the fluid to be discharged. Furthermore, the O-rings 133a, 133b, and 133c are formed of colored silicon, for example, to function as position markers for visually checking whether the piston 132 is in the first state or the second state. The cylinder 131 is transparent, in the same manner as the outward-facing surface of the external packaging member 110. Accordingly, the O-rings 133a, 133b, and 133c provided in the piston 132 can be seen from outside the external packaging member 110. Accordingly, by viewing the O-rings 133a, 133b, and 133c when the fluid transport cartridge 100 is mounted in the fluid transport driving unit 200, the user can check whether the piston 132 is in the first state or the second state. In other words, by viewing the O-rings 133a, 133b, and 133c, the user can check whether the fluid to be discharged is the first fluid or the second fluid.

The external packaging member 110 includes an insertion hole 160 near the fluid discharge portion 103 on the inward-facing surface of the third groove 123 that faces the fluid transport driving unit 200. A pressure detecting pin is inserted into the insertion hole 160 in order to measure pressure of the third elastic tube 113. Furthermore, the external packaging member 110 includes a cam-housing opening 150 serving as a position fixing member, along with the cam unit 210, at a position opposite the cam unit 210 serving as a position fixing member on the unit side when the external packaging member 110 is mounted on the fluid transport driving unit 200. The cam-housing opening 150 is a through-hole that contacts the periphery of the cam unit 210. The external packaging member 110 includes protrusions 115a and 115b, which protrude from the inward-facing surface near two corner regions located on a diagonal of the inward-facing surface that faces the fluid transport driving unit 200. The protrusions 115a and 115b engage with fastening holes provided in the fluid transport driving unit 200. In this way, positional misalignment between the fluid transport cartridge 100 and the fluid transport driving unit 200 is restricted. Furthermore, the external packaging member 110 includes a through-hole 152. A convex portion provided on the fluid transport driving unit 200 engages with the through-hole 152.

The pressing pins 140 are examples of a pressing portion that moves between a first position in which the third elastic tube 113 is pressed from the outside to constrict the fluid delivery path and a second position that does not constrict the fluid delivery path. The pressing pins 140 are arranged along a pin guiding groove 124 formed in the external packaging member 110. The pressing pins 140 are arranged along the third elastic tube 113 in the transport direction of the fluid, at uniform intervals in a radial manner centered on the rotational center of the cam unit 210. The tips of the pressing pins 140 protrude toward the cam-housing opening 150 in a direction toward the center of the cam-housing opening 150. Furthermore, the tips of the pressing pins 140 have semi-spherical surfaces oriented in a direction opposite the housing direction of the cam unit 210. By including such semi-spherical surfaces, when the cam unit 210 is housed in the cam-housing opening 150, friction between the tips of the pressing pins 140 and the side surface of the cam body 212 is decreased, and the pressing pins 140 can be arranged reliably at set positions.

Furthermore, when the pressing pins 140 arranged in the pin guiding groove 124 are seen from the outside, the tip portions of the pressing pins 140 are tapered to have a fine tip. In this way, the pressing pins 140 can be arranged radially in a small mounting space. Since the tips of the pressing pins 140 are tapered, the contact surface area between the cam body 212 and the pressing pins 140 is decreased, and the sliding resistance experienced when the cam body 212 is rotationally driven can be decreased. The cam-housing opening 150 is shaped as an arc centered on the rotational center of the cam unit 210. In this way, when the fluid transport cartridge 100 is mounted in the fluid transport driving unit 200, the center of the arc-shaped cam-housing opening 150 can be matched to the rotational center of the cam unit 210. Since the center of the arc-shaped cam-housing opening 150 is matched to the rotational center of the cam unit 210, when the cam unit 210 is rotationally driven while being housed in the cam-housing opening 150, positional misalignment between the fluid transport cartridge 100 and the cam unit 210 can be prevented. Furthermore, since the center of the arc-shaped cam-housing opening 150 is matched to the rotational center of the cam unit 210, the pressing pins 140 can sequentially press the third elastic tube 113 with a uniform force in response to the rotational drive of the cam body 212. Accordingly, in response to driving of the cam body 212, the pressing pins 140 can accurately press the third elastic tube 113. As a result, the precise set discharge amount of the fluid can be discharged.

In a state where the fluid transport cartridge 100 is mounted in the fluid transport driving unit 200, the pressing pins 140 move between the first position in which the third elastic tube 113 is pressed from the outside in the radial direction to constrict the fluid delivery path and the second position that does not constrict the fluid delivery path, thereby delivering fluid from the upstream side to the downstream side, according to the driving of the cam body 212. In other words, in response to the driving of the cam body 212, the pressing pins 140 sequentially press the third elastic tube 113 from the upstream side to the downstream side, thereby causing the third elastic tube 113 to move peristaltically and deliver the fluid from the upstream side to the downstream side.

On the other hand, when the fluid transport cartridge 100 is removed from the fluid transport driving unit 200, i.e. when the cam-housing opening 150 is not housing the cam unit 210, the pressing pins 140 do not press on the third elastic tube 113. In other words, when the cam-housing opening 150 is not housing the cam unit 210, the pressing pins 140 are located at the second position in which the elastic force of the third elastic tube 113 causes the fluid path to not be constricted. In this way, when the fluid transport apparatus 300 is not being used, by removing the fluid transport cartridge 100 from the fluid transport driving unit 200, the third elastic tube 113 can be kept in a state of not being pressed upon by any of the pressing pins 140. Accordingly, by maintaining the state in which the third elastic tube 113 is not being pressed upon by any of the pressing pins 140, wear and tear on the third elastic tube 113 can be prevented from progressing.

The cam unit 210, which is the drive mechanism causing the pressing pins 140 to exert pressure, is provided in fluid transport driving unit 200. The cam unit 210 should rotate accurately in order to accurately discharge the set discharge amount of fluid. If the cam unit 210 is provided in the fluid transport cartridge 100, the cam unit 210 should be accurately fixed at a predetermined position every time the fluid transport cartridge 100 is worn. However, it is difficult to accurately fix the cam unit 210 at the predetermined position. Therefore, by providing the cam unit 210 in the fluid transport driving unit 200, positional misalignment of the cam unit 210 occurring every time the fluid transport cartridge 100 is worn can be prevented. In this way, variations in the fluid discharge amount every time the fluid transport cartridge 100 is worn can be prevented.

The fluid transport cartridge 100 can be attached to and detached from the fluid transport driving unit 200. Therefore, the fluid transport cartridge 100 is a consumable product that can be replaced as needed. Accordingly, by replacing the fluid transport cartridge 100 after a set number of uses, for example, the cleanliness of the fluid transport cartridge 100 can be maintained.

Figure 4A:
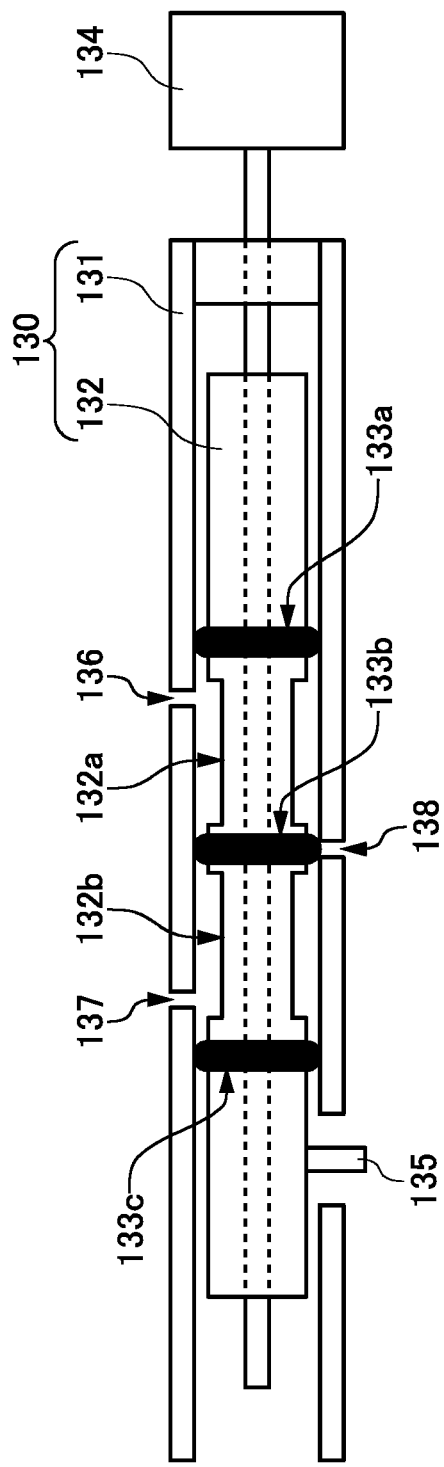
FIG. 4A is a schematic view for describing switching of the fluid by the switching valve.
Figure 4B:
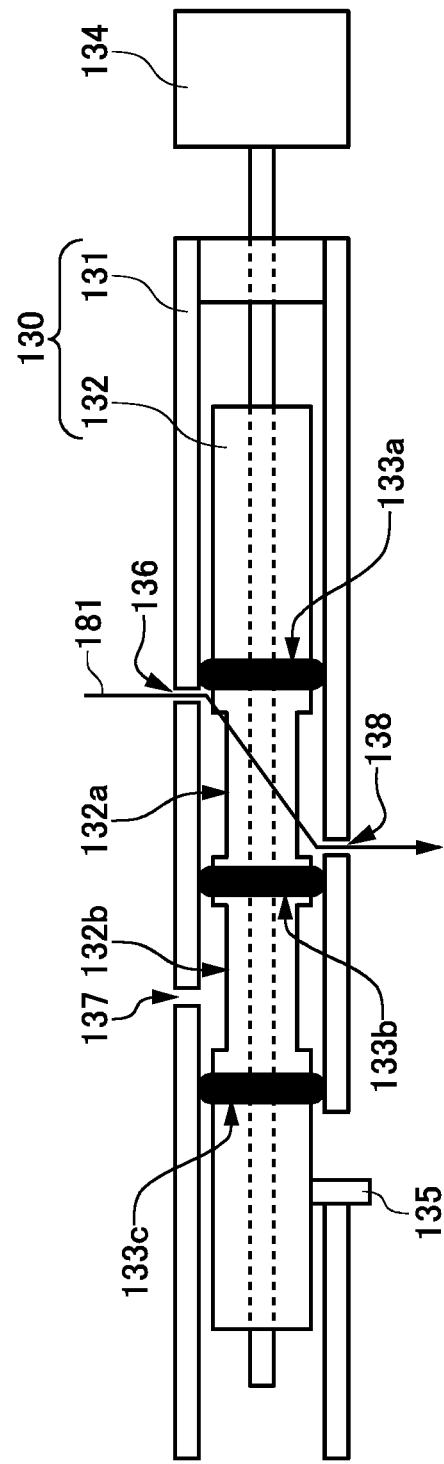
FIG. 4B is a schematic view for describing switching of the fluid by the switching valve.
Figure 4C:
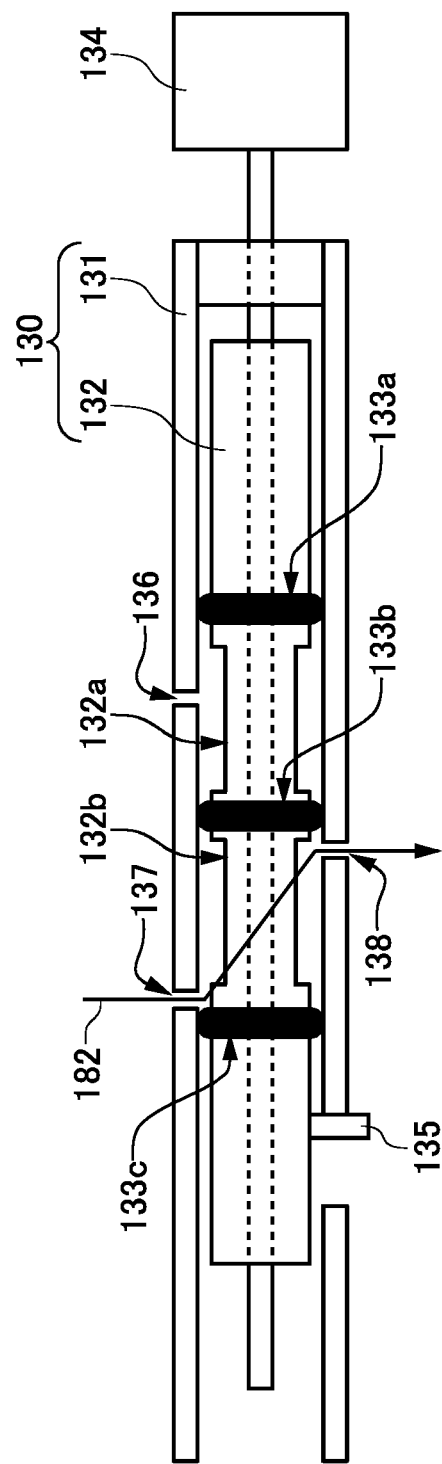
FIG. 4C is a schematic view for describing switching of the fluid by the switching valve.

FIGS. 4A, 4B, and 4C are schematic views that describe switching of the fluid in the switching valve 130. The cylinder 131 includes a first flow path opening 136 connected to the first fluid path, a second flow path opening 137 connected to a second fluid path, and a third flow path opening 138 connected to a third fluid path. The piston 132 includes an arc-shaped first fluid path groove 132a along the periphery thereof between the O-ring 133a and the O-ring 133b, and a second fluid path groove 131b between the o-ring 133b and the o-ring 133b.

As shown in FIG. 4A, the first flow path opening 136, the second flow path opening 137, and the third flow path opening 138 are separated by the O-rings 133a, 133b, and 133c, and when the first fluid path groove 132a and the second fluid path groove 132b are not at positions opposite each other, neither the first fluid path nor the second fluid path is connected to the third fluid path. Accordingly, neither the first fluid nor the second fluid is discharged to the third fluid path. On the other hand, as shown in FIG. 4B, when the piston 132 and the O-rings 133a, 133b, and 133c slide within the cylinder 131 such that the first fluid path groove 132a moves to a position opposite the first flow path opening 136 and the third flow path opening 138, i.e. when the first flow path opening 136 and the third flow path opening 138 are positioned between the o-ring 133a and the o-ring 133b, the first fluid path and the third fluid path are connected. Therefore, the first fluid is discharged from the first fluid path to the third fluid path, as shown by the arrow 181. In other words, the state of the piston 132 and the O-rings 133a, 133b, and 133c shown in FIG. 4B is an example of the first state in which the first fluid is guided from the first elastic tube 111 to the third elastic tube 113. Furthermore, as shown in FIG. 4C, when the piston 132 slides in the cylinder 131 such that the second fluid path groove 132b moves to a position opposite the second flow path opening 137 and the third flow path opening 138, i.e. when the second flow path opening 137 and the third flow path opening 138 are at positions between the O-ring 133b and the O-ring 133c, the second fluid path and the third fluid path are connected. In this way, the second fluid is discharged from the second fluid path to the third fluid path, as shown by the arrow 182. In other words, the state of the piston 132 and the O-rings 133a, 133b, and 133c shown in FIG. 4C is an example of the second state in which the second fluid is guided from the second elastic tube 112 to the third elastic tube 113.

Figure 4D:
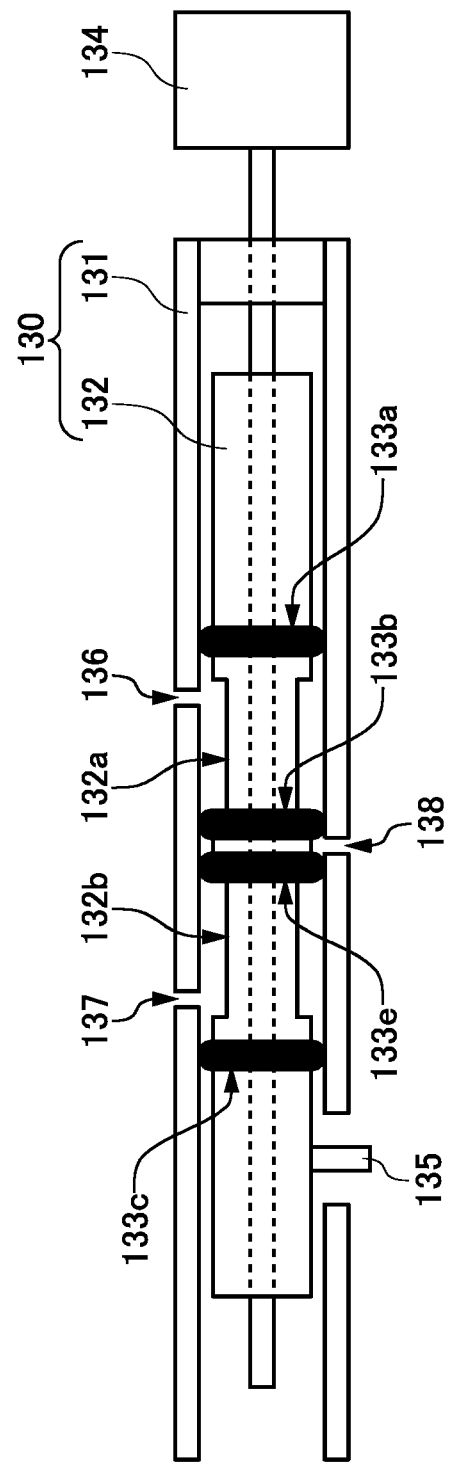
FIG. 4D is a schematic view for describing a modification of switching of the fluid by the switching valve.

The detector 135 that is provided to the piston 132 and protrudes outward from the cylinder 131 moves according to the movement of the piston 132, as shown in FIGS. 4A, 4B, and 4C. Accordingly, by detecting the position of the detector 135 using the position sensor, the position of the piston 132 can be detected. As shown in FIG. 4D, the switching valve 130 may include the O-rings 133a, 133b, 133c, and 133d, and the piston 132 may include the arc-shaped first fluid path groove 132a between the o-ring 133a and the o-ring 133b along the periphery thereof and the second fluid path groove 131b between the o-ring 133c and the o-ring 133d. Furthermore, the switching valve 130 may be configured to include a check valve structure within the first fluid path and the second fluid path.

Figure 5:
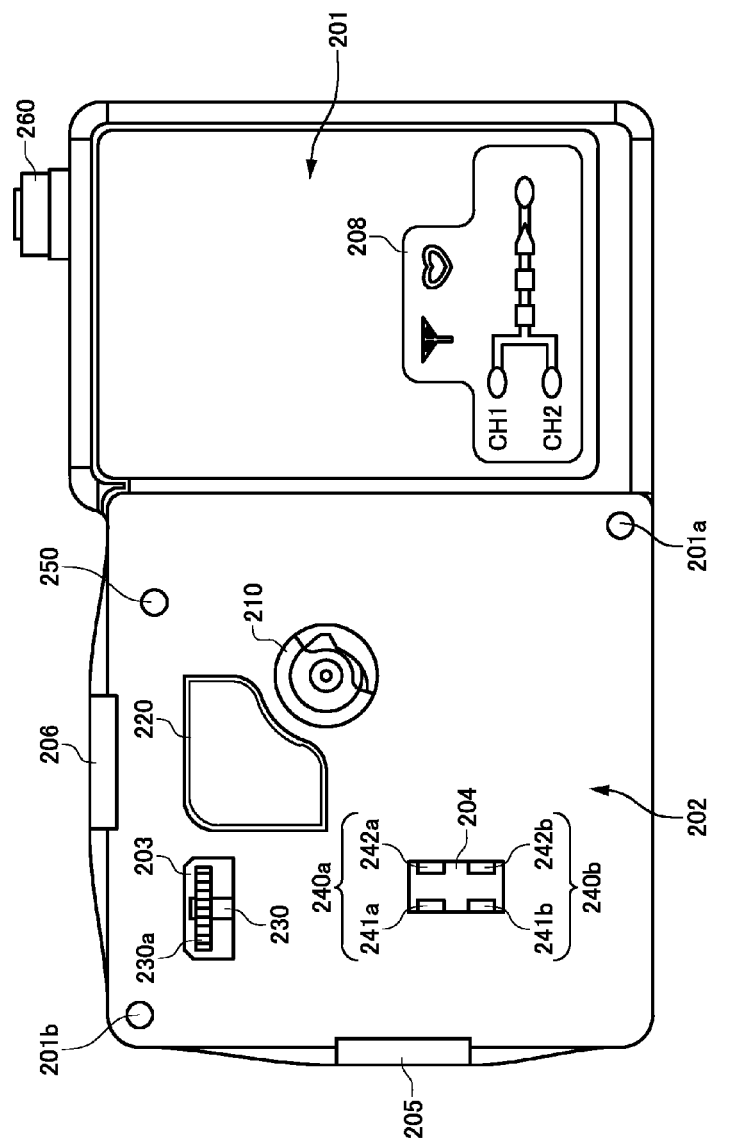
FIG. 5 is an overhead view of the fluid transport driving unit.

FIG. 5 is an overhead view of the fluid transport driving unit 200. The top surface of the fluid transport driving unit 200 includes an attachment surface 202 where the fluid transport cartridge 100 is mounted and a display surface 201 with a LED display section 208 displaying information concerning the fluid to be discharged, the drive state of the fluid transport driving unit 200, and the like. The attachment surface 202 is positioned lower than the display surface 201. In other words, the display surface 201 protrudes upward beyond the attachment surface 202. Furthermore, the attachment surface 202 includes the cam unit 210 protruding therefrom. The attachment surface 202 also includes a protruding arc-shaped convex portion 220, in which the circle of the arc is centered on the rotational center of the cam unit 210. When the fluid transport cartridge 100 is mounted on the attachment surface 202, the outward-facing surface of the fluid transport cartridge 100 and the display surface 201 are in substantially the same plane. The fluid transport driving unit 200 includes, in the attachment surface 202, fastening holes 201a and 201b that engage respectively with the protrusions 115a and 115b provided on the fluid transport cartridge 100. The fluid transport driving unit 200 may have a packing rubber sheet formed of silicon rubber, for example, on the attachment surface 202. The packing rubber sheet functions as packaging between the attachment surface of the fluid transport driving unit 200 and the inward-facing surface of the fluid transport cartridge 100 when the fluid transport cartridge 100 is mounted in the fluid transport driving unit 200. In this way, the packing rubber sheet provides the fluid transport driving unit 200 with a drip-proof function.

The fluid transport driving unit 200 includes a drive axle 230. The drive axle 230 includes a gear 230a that engages with a gear of the threaded shaft 134. The gear 230a of the drive axle 230 is exposed to the outside through a gear opening 203 formed in the attachment surface 202 of the fluid transport driving unit 200. The fluid transport driving unit 200 also includes position sensors 240a and 240b for detecting the position of the piston 132. The position sensors 240a and 240b are exposed to the outside through a sensor opening 204 formed in the attachment surface 202 of the fluid transport cartridge 100. The position sensor 240a or 240b may be formed by a photo interrupter and include a light emitting section 241a or 241b and a light receiving section 242a or 242b. The light emitted by the light emitting section 241a or 241b may be infrared light or visible light, for example, and is received by the light receiving section 242a or 242b. The position of the piston 132 is detected according to the reception state of the light received by the light receiving section 242a or 242b. For example, if the light emitted by the light emitting section 241a is blocked by the detector 135 and cannot reach the light receiving section 242a, the piston 132 is in the first state. On the other hand, if the light emitted by the light emitting section 241b is block by the detector 135 and cannot reach the light receiving section 242b, the piston 132 is in the second state. Accordingly, the piston 132 is determined to be in the first state or the second state based on the whether the light receiving section 242a or the light receiving section 242b receive light.

The fluid transport driving unit 200 includes a pressure-detecting pin 250 that derives pressure of the third elastic tube 113. The pin 250 protrudes from the attachment surface 202. When the fluid transport cartridge 100 is mounted, the tip of the pin 250 contacts the third elastic tube 113 through an insertion hole 160 formed in the external packaging member 110 of the fluid transport cartridge 100. In this way, the pin 250 communicates, to the pressure sensor located within the fluid transport driving unit 200, the stress corresponding to the internal force in the third elastic tube 113. The pressure sensor indirectly measures the pressure of the fluid flowing within the third elastic tube 113, based on the stress. In other words, the pressure sensor measures the internal pressure in the third elastic tube 113 occurring when the pump discharges, based on the stress.

Figure 6A:
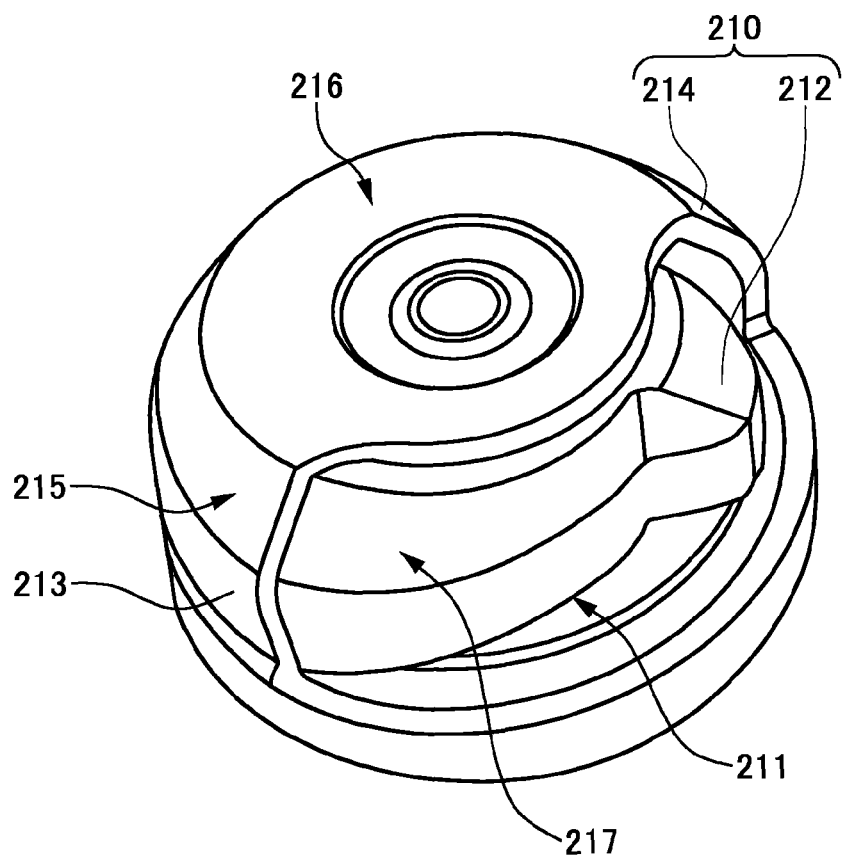
FIG. 6A is a perspective view of the cam of the fluid transport driving unit.
Figure 6B:
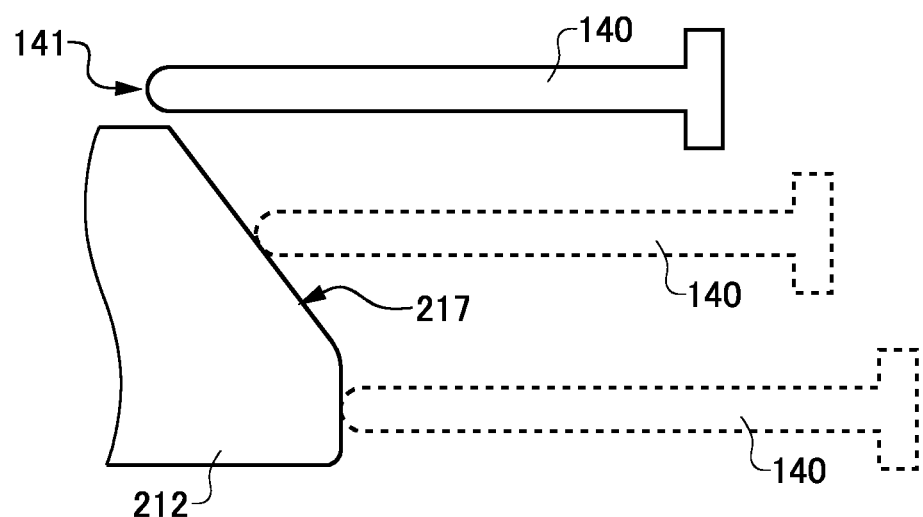
FIG. 6B is a schematic view for describing a tapered surface of the cam body and semi-spherical surface of a pressing pin.

FIG. 6A is a perspective view of the cam unit 210 of the fluid transport driving unit 200. The cam unit 210 includes a cam body 212 and a cam cover 214. The cam body 212 sequentially presses the plurality of pressing pins 140. The cam cover 214 covers a portion of the cam body 212. The cam cover 214 includes a cam opening 211, and the cam body 212 is exposed through the cam opening 211. The cam body 212 contacts the pressing pins 140 in the portion exposed by the cam opening 211. When the fluid transport cartridge 100 is mounted on the fluid transport driving unit 200, the peripheral outer surface 213 of the cam cover 214 engages with the inner peripheral surface of the cam-housing opening 150. As a result, the cam unit 210 is fixed to the fluid transport cartridge 100. Furthermore, the peripheral outer surface 213 of the cam cover 214 has a tapered surface 215 at which the diameter of the peripheral outer surface 213 decreases in a direction toward the top surface 216 of the cam cover 214. By providing the cam cover 214 with the tapered surface 215 in this manner, the cam unit 210 can be easily housed in the cam-housing opening 150. The peripheral outer surface of the cam body 212 has a tapered surface 217 along the tapered surface 215 of the cam cover 214. Furthermore, as described above, the tips 141 of the pressing pins 140 have semi-spherical surfaces facing the housing direction of the cam unit 210. By using the tapered structure for the cam body 212 and the semi-spherical structure for the pressing pins 140 in this manner, when the cam unit 210 is housed in the cam-housing opening 150, while pressing the pressing pins 140 along the tapered surface 217 of the cam body 212 and maintaining the pressing pins 140 in a parallel state with respect to the inward-facing surface of the fluid transport cartridge 100, the pressing pins 140 can easily slide in a radial manner relative to the rotational center of the cam unit 210, as shown in FIG. 6B. As a result, the fluid transport cartridge 100 can be easily attached and detached. Furthermore, when the fluid transport cartridge 100 is mounted in the fluid transport driving unit 200, the pressing pins 140 can be arranged accurately at the set positions.

Figure 7:
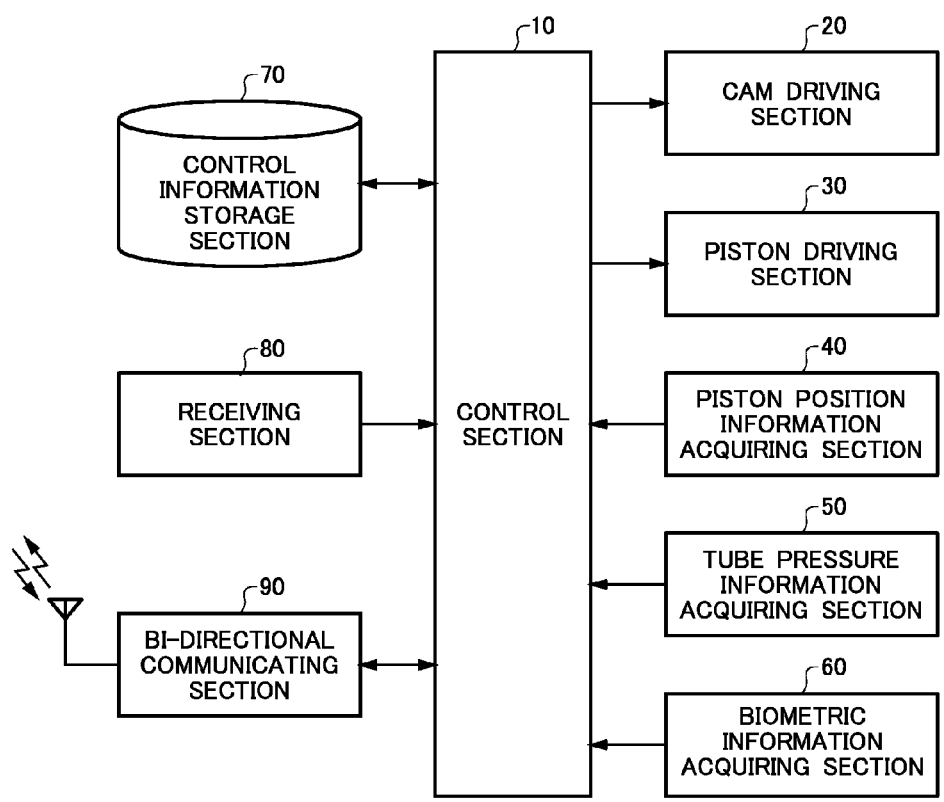
FIG. 7 shows function blocks of the fluid transport driving unit.

FIG. 7 shows function blocks of the fluid transport driving unit 200. The fluid transport driving unit 200 includes a control section 10, a cam driving section 20, a piston driving section 30, a piston position information acquiring section 40, a tube pressure information acquiring section 50, a biometric information acquiring section 60, a control information storage section 70, a receiving section 80, and a bi-directional communicating section 90.

The cam driving section 20 operates the cam body 212 to transport to the fluid discharge portion 103 the fluid that fills the fluid paths of the mounted fluid transport cartridge 100. When switching the fluid to be discharged, the piston driving section 30 operates the drive axle 230 to slide the piston 132 of the switching valve 130. The cam driving section 20 and the piston driving section 30 may be stepping motors or geared motors.

The piston position information acquiring section 40 acquires a reception state of light, such as infrared rays, from the position sensors 240a and 240b, in order to acquire the position information of the piston 132 indicating whether the piston 132 is in the first state or the second state. The tube pressure information acquiring section 50 acquires the pressure information relating to the internal pressure of the third elastic tube 113, via the pressure-detecting pin 250. The biometric information acquiring section 60 acquires biometric information such as information relating to the blood pressure, the blood sugar level, or an electrocardiogram of the test animal via the input terminal 260. The biometric information acquiring section 60 may acquire the biometric information wirelessly. The control information storage section 70 stores control information such as setting conditions to be referenced by the control section 10 to output a piston drive signal or a cam drive signal to the piston driving section 30 or the cam driving section 20. The setting conditions include conditions such as discharge start time, a discharge ratio indicating the discharge amount per unit time, discharge duration, and discharge interval. The setting conditions are set for each of the first fluid and the second fluid. The receiving section 80 functions as an external connection terminal, and receives input such as the setting conditions from an external input apparatus, such as a personal computer. The bi-directional communicating section 90 performs wireless bi-directional communication with an external wireless terminal. The setting conditions may be received wirelessly from the external wireless terminal through the bi-directional communicating section 90. The bi-directional communicating section 90 may wirelessly transmit, to the external wireless terminal, information relating to the setting conditions or biometric information, for example.

The control section 10 outputs the piston drive signal to the piston driving section 30 in order to align the position of the piston 132 with the fluid path of the fluid to be discharged, based on the setting conditions. The control section 10 determines whether the piston 132 is at the position of the fluid path of the fluid to be discharged based on the position information of the piston 132 acquired through the piston position information acquiring section 40. When the piston 132 is at the position of the fluid path of the fluid to be discharged, the control section 10 outputs the cam drive signal to the cam driving section 20, in order to cause the amount of fluid according to the setting conditions to be discharged. In this way, the fluid transport apparatus 300 can selectively output set discharge amounts for two types of fluids. For example, the fluid transport apparatus 300 can selectively discharge two types of medicinal liquids. After the set discharge amount of a first type of medicinal liquid is discharged, the fluid transport apparatus 300 can flush out the transport path connected to the fluid discharge portion 103 of the fluid transport cartridge 100 by discharging a set discharge amount of a saline solution.

The control section 10 acquires the outputs measured by the pressure sensor and the pressure-detecting pin 250, via the tube pressure information acquiring section 50, and controls the cam driving section 20 based on the acquired outputs. For example, when a blood vessel of the test animal being injected with the fluid is obstructed, the control section 10 must stop the discharge of fluid. Therefore, the control section 10 monitors the pressure state of the third elastic tube 113 based on the pressure information from the tube pressure information acquiring section 50. When the pressure of the third elastic tube 113 is greater than or equal to a predetermined threshold value, the control section 10 determines that some kind of abnormality has occurred, such as the blood vessel of the test animal being injected with the fluid becoming obstructed, and stops the discharge of fluid.

The fluid discharge amount discharged by the fluid transport apparatus 300 depends on the inner diameter of the third elastic tube 113 mounted in the fluid transport cartridge 100, for example. However, the inner diameter of the third elastic tube 113 has variations. The internal diameter also has variations according to the state of the mounted fluid transport cartridge 100. In other words, each fluid transport cartridge 100 has a different inner diameter. Accordingly, even when the rotation amount of the cam body 212 is the same, the fluid discharge amount discharged by the fluid transport apparatus 300 differs according to the fluid transport cartridge 100. Therefore, in order to maintain accuracy of the fluid discharge amount discharged by the fluid transport apparatus 300, the setting conditions are preferably corrected for each fluid transport cartridge 100.

To this end, the receiving section 80 or the bi-directional communicating section 90 receive characteristic values of the mounted fluid transport cartridge 100. The characteristic values are correction values set for each fluid transport cartridge 100 in order to correct variation in the fluid discharge amount for the drive amount of the cam driving section 20. The characteristic values are correction values that correct the variation based on individual variation in components of the fluid transport cartridge 100, such as the third elastic tube 113. The characteristic values may be set by having the fluid transport apparatus 300 actually operate, measuring the fluid discharge amount discharged by the fluid transport apparatus 300 having the set setting conditions, and comparing the set discharge amount to the measured discharge amount. The cam driving section 20 acquires the characteristic values via the control section 10, and corrects the rotation amount of the cam body 212 based on the characteristic values. In this way, the control items from the control section 10 can be simplified, and problems resulting from errors in the discharge amount can easily be discovered. The correction values based on the characteristic values may be generated in the control section 10, and the control section 10 may output the corrected cam drive signal to the cam driving section 20.

For example, the total number of pulses to be output to the cam driving section 20 per unit time according to the set discharge amount can be set in advance. In this case, the control section 10 corrects the number of pulses per unit time corresponding to the set discharge amount, based on the characteristic values. The control section 10 then outputs to the cam driving section 20, which is a stepping motor, a cam drive signal corresponding to the corrected total number of pulses. In this way, the rotation amount of the cam body 212 can be adjusted according to individual variation in the fluid transport cartridges 100. Accordingly, variation in the discharge amount for each fluid transport cartridge 100 can be restricted.

The control information storage section 70 may store a discharge amount table or discharge amount function indicating the total number of pulses to be output per unit time according to the discharge amount. The control information storage section 70 may store a correction table or correction function indicating a correction coefficient or correction number of pulses corresponding to the characteristic values. When the receiving section 80 receives the characteristic values of the mounted fluid transport cartridge 100, the control section 10 may correct the total number of pulses per unit time corresponding to the set discharge amount, based on the received characteristic values, the discharge amount function or discharge amount table, and the correction function or correction table, and output to the cam driving section 20 the cam drive signal corresponding to the corrected total number of pulses.

Figure 8:
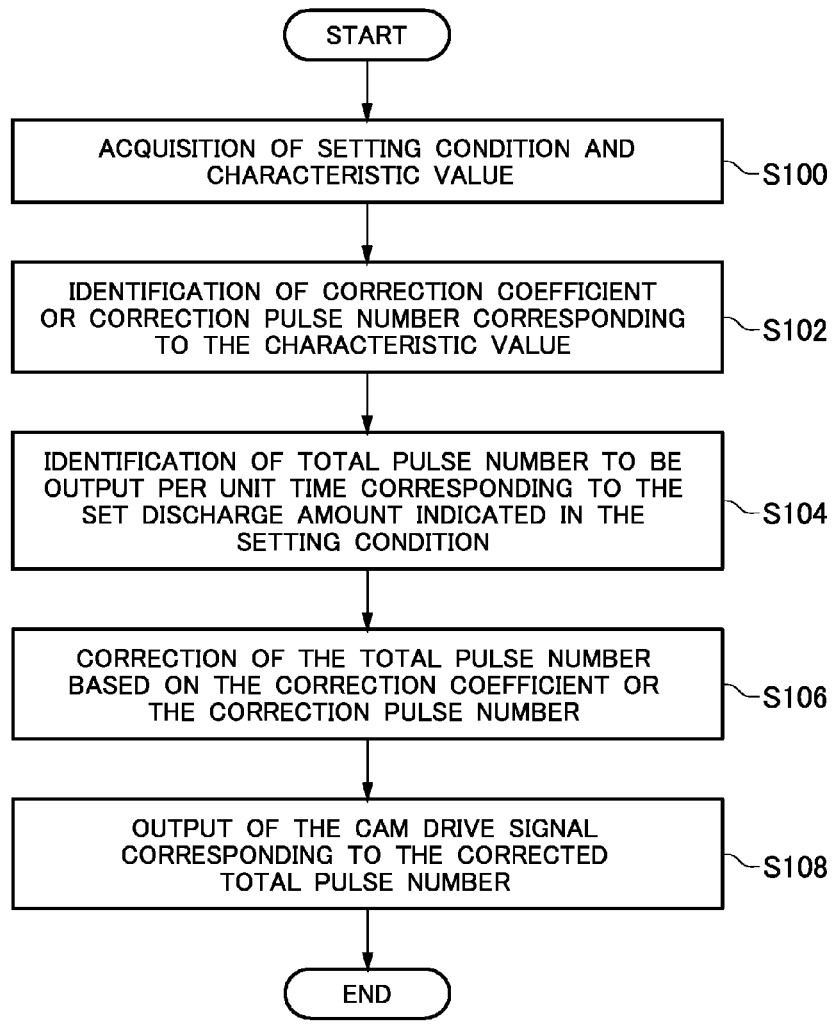
FIG. 8 is a flow chart for the fluid discharge control performed by the control section.

FIG. 8 is a flow chart for the fluid discharge control performed by the control section 10. The control section 10 acquires the setting conditions and characteristic values of the equipped fluid transport cartridge 100 via the receiving section 80 (S100). The user may provide the control section 10 with the characteristic values through the receiving section 80, by inputting a prescribed digit number from among identification numbers allocated to the fluid transport cartridge 100, for example. Next, the control section 10 references the correction function or correction table stored in the control information storage section 70, and identifies the correction number of pulses or correction coefficient corresponding to the characteristic value (S102). Furthermore, the control section 10 references the discharge amount function or discharge amount table stored in the control information storage section 70, and identifies the total number of pulses to be output per unit time corresponding to the set discharge amount shown in the setting conditions (S104). In addition, the control section 10 corrects the identified total number of pulses, based on the identified correction number of pulses or correction coefficient (S106). For example, the control section 10 corrects the total number of pulses by adding or subtracting the correction number of pulses to or from the total number of pulses. As another example, the control section 10 may correct the total number of pulses by multiplying the total number of pulses by the correction coefficient. As yet another example, the control section 10 may correct the total number of pulses by subtracting, adding, or multiplying the correction coefficient from, to, or by a coefficient included in the discharge function for calculating the total number of pulses. The control section 10 outputs to the cam driving section 20 a cam drive signal corresponding to the corrected total number of pulses (S108). In this way, the accuracy of the fluid discharge amount discharged by the fluid transport apparatus 300 can be maintained.

The control section 10 may control the fluid discharge based on the biometric information acquired via the biometric information acquiring section 60. For example, the control section 10 may periodically acquire blood pressure information relating to the blood pressure of the test animal, as biometric information. The control section 10 controls the discharge amount and discharge timing of medicinal liquid that lowers blood pressure, such that the blood pressure of the test animal remains constant, based on the blood pressure information. In this way, the fluid transport apparatus 300 can control the dosing of medicinal liquid according to change in the biological response of the test animal. The biometric information may include a variety of physical amounts such as bioelectric potential, blood flow, body temperature, and acceleration. The bi-directional communicating section 90 may wirelessly transmit the acquired biometric information to the external wireless terminal.

The fluid transport driving unit 200 according to the present embodiment may be configured to have a control program installed therein for performing each of the processes relating to fluid discharge described above, and to have this control program executed by a computer. In other words, the fluid transport driving unit 200 may be configured by causing a computer to function as the control section 10, the piston position information acquiring section 40, the tube pressure information acquiring section 50, the biometric information acquiring section 60, the control information storage section 70, and the receiving section 80 as a result of executing the control program for performing each of the processes relating to fluid discharge. As another example, the fluid transport driving unit 200 may be controlled by wireless communication commands form the outside.

The computer includes a CPU, an interface, a communication bus, and various memories such as a ROM, a RAM, and an EEPROM (registered trademark), and may function as the fluid transport driving unit 200 by having the CPU read and sequentially execute the processing program stored in the ROM in advance as firmware.

According to the fluid transport apparatus 300 of the present embodiment described above, reservoirs for two types of fluid can be set, and setting conditions such as discharge amount, discharge speed, and discharge time can be set respectively for each fluid type. The setting conditions can be wirelessly transmitted to the fluid transport apparatus 300 by remote control, as needed.

The fluid transport cartridge 100 can be attached to and detached from the fluid transport driving unit 200. Accordingly, the fluid transport cartridge 100 filled with medicinal liquid or the like can be replaced as needed, and therefore the fluid transport cartridge 100 can always be kept clean. When replacing only the elastic tube due to wear and tear, the tension in the elastic tube changes according to the arrangement state of the elastic tube, and so there is a chance that the inner diameter of the elastic tube will also change. However, with the present embodiment, exchange of the elastic tube can be realized by exchanging the fluid transport cartridge 100 in a state where the elastic tube is already arranged. The fluid discharge amount can then be corrected based on the set characteristic values for each fluid transport cartridge 100. Accordingly, the occurrence of errors in the fluid discharge amount caused by individual variation in the inner diameter of the elastic tubes in the fluid transport cartridges 100 can be prevented.

In addition, the cam unit 210 is provided on the fluid transport driving unit 200 side. Accordingly, when the fluid transport cartridge 100 is removed from the fluid transport driving unit 200, the third elastic tube 113 is not pressed on by the pressing pins 140 as a result of the pressing pins 140 being pressed by the cam body 212. Accordingly, wear and tear of the third elastic tube 113 caused by deformation or compression by the pressing pins 140 can be restricted. As a result, the occurrence of errors in the fluid discharge amount can be restricted.

Furthermore, by providing semi-spherical surfaces on the tips of the pressing pins 140 and tapered surfaces on the side surface of the cam body 212, the fluid transport cartridge 100 can be easily attached and detached. In this way, exchange of the fluid transport cartridge 100 can be performed more quickly, and therefore the burden placed on the test animal can be decreased. As a result, when exchanging the fluid transport cartridge 100, reduction to the accuracy of the experimental results caused by the test animal being unable to remain relaxed can be prevented.

The switching of the fluid is realized by a piston configuration that includes grooves formed for each fluid. Accordingly, contamination of the solution in the reservoirs caused by fluid switching can be prevented.

In the above embodiment, the pressing portion need not be formed by a plurality of pressing pins 140. Instead of the pressing pins, for example, a cam having a shape enabling movement between a first position in which the fluid delivery path is constricted by pressing from the outside of the elastic tube and a second position that does not constrict the fluid delivery path may be used. Furthermore, the third elastic tube 113 may be arranged in a straight line, and a plurality of pressing pins 140 may be arranged in a straight line along this third elastic tube 113. In this case, the pressing pins 140 may be sequentially pressed by spiral protrusions formed on the outer periphery of a cylindrical rotational axis.

While the embodiment of the present invention has been described, the technical scope of the invention is not limited to the above described embodiment. It is apparent to persons skilled in the art that various alterations and improvements can be added to the above-described embodiment. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

LIST OF REFERENCE NUMERALS

10: control section, 20: cam driving section, 30: piston driving section, 40: piston position information acquiring section, 50: tube pressure information acquiring section, 60: biometric information acquiring section, 70: control information storage section, 80: receiving section, 90: bi-directional communicating section, 100: fluid transport cartridge, 101: first fluid inflow portion, 102: second fluid inflow portion, 103: fluid discharge portion, 110: external packaging member, 111: first elastic tube, 112: second elastic tube, 113: third elastic tube, 130: switching valve, 140: pressing pin, 150: cam-housing opening, 160: insertion hole, 200: fluid transport driving unit, 205: first hook, 206: second hook, 210: cam unit, 250: pin, 300: fluid transport apparatus

What is claimed is:

1. A fluid transport driving unit comprising:
a drive mechanism including a cam body;
a driving section that causes the drive mechanism to operate to transport fluid filling a transport path of a fluid transport cartridge to a discharge opening of the transport path;
a receiving section that receives a characteristic value from among a plurality of characteristic values respectively measured in advance for each of a plurality of the fluid transport cartridges, the characteristic values being correction values for correcting variation based on individual differences among elastic tubes forming the transport paths;
a control section that controls the driving section based on the characteristic value received by the receiving section; and
a position fixing member having a convex portion that protrudes from an attachment surface of the fluid transport driving unit and has an arc shape with a circle of the arc being centered on a rotational center of the cam body, wherein
the fluid transport cartridge is attachable to and detachable from the fluid transport driving unit, the cam body protrudes from the attachment surface and moves a pressing pin of the fluid transport cartridge pressing the elastic tube from the outside, when the fluid transport cartridge is attached to the fluid transport driving unit, the cam body is housed in a cam-housing opening of the fluid transport cartridge and the convex portion engages with a through-hole of the fluid transport cartridge such that the position fixing member fixes the position of the cam body relative to the pressing pin, and the control section controls a rotation amount of the cam body based on the correction value.

2. The fluid transport driving unit according to claim 1, wherein the characteristic values are correction values for correcting variation in discharge amount of the fluid with respect to a driving amount of the driving section.

3. The fluid transport driving unit according to claim 1, comprising a pressure sensor that measures pressure of the elastic tube.

4. The fluid transport driving unit according to claim 3, wherein the control section controls the driving section based on output of the pressure sensor.

5. The fluid transport driving unit according to claim 1, comprising a biometric information acquiring section that acquires biometric information of a subject to which the fluid transport driving unit is attached, wherein the control section controls the driving section based on the biometric information.

6. The fluid transport driving unit according to claim 1, comprising a communicating section that wirelessly acquires a setting condition for controlling the driving section, wherein the control section controls the driving section based on the setting condition.

7. A non-transitory computer readable medium storing thereon a program for controlling a fluid transport driving unit, the program causing a computer to perform operations comprising:

receiving a characteristic value from among a plurality of characteristic values respectively measured in advance for each of a plurality of fluid transport cartridges, the fluid transport cartridges each being attachable to and detachable from the fluid transport driving unit and having a transport path and a discharge opening, and the characteristic values being correction values for correcting variation based on individual differences among elastic tubes forming the transport paths; and controlling, based on the received characteristic value, a rotation amount of a cam body included in a drive mechanism of the fluid transport driving unit to move a pressing pin of an attached fluid transport cartridge pressing the elastic tube from the outside, which causes the drive mechanism to operate to transport fluid filling the transport path of the attached fluid transport cartridge to the discharge opening, wherein each of the plurality of fluid transport cartridges includes a position fixing member having a convex portion that protrudes from an attachment surface of the fluid transport driving unit and has an arc shape with a circle of the arc being centered on a rotational center of the cam body, and when a fluid transport cartridge is attached to the fluid transport driving unit, the cam body is housed in a cam-housing opening of the fluid transport cartridge and the convex portion engages with a through-hole of the fluid transport cartridge such that the position fixing member fixes the position of the cam body relative to the pressing pin.

* * * * *